United States Patent
Crameri et al.

(10) Patent No.: US 6,830,891 B1
(45) Date of Patent: Dec. 14, 2004

(54) METHODS FOR DIAGNOSIS OF ALLERGIC BRONCHOPULMONARY ASPERGILLOSIS

(75) Inventors: Reto Crameri, Davos-Platz (CH); Stefanie Hemmann, Davos Platz (CH); Kurt Blaser, Davos-Platz (CH)

(73) Assignee: Pharmacia Diagnostics AB, Uppsala (SE)

( * ) Notice: Subject to any disclaimer, the term of this patent is extended or adjusted under 35 U.S.C. 154(b) by 0 days.

(21) Appl. No.: 09/319,806

(22) PCT Filed: Dec. 19, 1997

(86) PCT No.: PCT/SE97/02172

§ 371 (c)(1),
(2), (4) Date: Aug. 19, 1999

(87) PCT Pub. No.: WO98/28624

PCT Pub. Date: Jul. 2, 1998

(30) Foreign Application Priority Data

Dec. 20, 1996 (SE) .............................. 9604815

(51) Int. Cl.$^7$ .............................. G01N 33/53
(52) U.S. Cl. ................ 435/7.1; 435/7.31; 424/9.1; 424/9.81
(58) Field of Search ................. 435/7.1, 7.31; 424/9.1, 9.81

(56) References Cited

PUBLICATIONS

Colman et al. Research in Immunology, vol. 145 pp. 33–36, 1994.*
Banerjee et al., Asian Pacific Journal of Allergy and Immunology, (1990) 8:13–18.
Moser et al., The Journal of Allergy and Clinical Immunology, (1994) 93(1(1)):1–11.
Little et al., The Journal of Allergy and Clinical Immunology, (1996) 98(1):55–63.

* cited by examiner

Primary Examiner—Patrick J. Nolan
(74) Attorney, Agent, or Firm—Dinsmore & Shohl LLP

(57) ABSTRACT

Methods for the diagnosis of ABPA in a human individual comprise determining if the individual carries antibodies reactive with one or more ABPA-related recombinant allergens, which one or more ABPA-related recombinant allergens discriminate between ABPA and allergic sensitization to *A. fumigatus*. Suitable allergens include rAsp F4, rAsp F6, rAsp F8, and ABPA-related fragments thereof which bind with IgE or IgG antibody.

17 Claims, No Drawings

SEQUENCE LISTING

<160> NUMBER OF SEQ ID NOS: 8

<210> SEQ ID NO 1
<211> LENGTH: 624
<212> TYPE: DNA
<213> ORGANISM: Artificial Sequence
<220> FEATURE:
<223> OTHER INFORMATION: Description of Artificial Sequence: recombinant allergen rAsp f6

<400> SEQUENCE: 1

```
caatacacgc tcccacccct ccctacccc tacgatgccc tccaaccta catctcccaa      60 cagatcatgg agctgcacca caaaaagcac catcaaacct acgtcaatgg cctgaatgcc    120
gcactcgagg cgcagaagaa agcggcggaa gccaacgacg tccccaagct cgtctccgtg    180
cagcaagcga tcaaattcaa cggcgggggg cacatcaacc attccctctt ctggaagaat    240
ctggccccgg agaaatccgg gggtggcaag atcgatcagg caccggtcct caaagcagcc    300
atcgagcagc gttggggatc cttcgataag ttcaaggatg ctttcaacac gaccctgctg    360
ggcattcagg gcagcggatg gggttggtta gtgaccgacg gacccaaggg aaagctagac    420
attaccacaa cccacgacca ggatccggtg accggggcgg cccccgtctt tggggtggat    480
atgtgggagc atgcttacta ccttcagtac ttgaacgaca agcctcgta tgccaagggc    540 atctggaacg tgatcaactg ggctgaagcg gagaatcggt acatagcggg tgacaagggt    600
ggacacccat tcatgaagct gtga                                          624
```

<210> SEQ ID NO 2
<211> LENGTH: 207
<212> TYPE: PRT
<213> ORGANISM: Artificial Sequence
<220> FEATURE:
<223> OTHER INFORMATION: Description of Artificial Sequence: recombinant allergen rAsp f6

<400> SEQUENCE: 2

```
Gln Tyr Thr Leu Pro Pro Leu Pro Tyr Pro Tyr Asp Ala Leu Gln Pro
  1               5                  10                  15

Tyr Ile Ser Gln Gln Ile Met Glu Leu His His Lys Lys His His Gln
             20                  25                  30

Thr Tyr Val Asn Gly Leu Asn Ala Ala Leu Glu Ala Gln Lys Lys Ala
         35                  40                  45

Ala Glu Ala Asn Asp Val Pro Lys Leu Val Ser Val Gln Gln Ala Ile
     50                  55                  60

Lys Phe Asn Gly Gly His Ile Asn His Ser Leu Phe Trp Lys Asn
 65                  70                  75                  80

Leu Ala Pro Glu Lys Ser Gly Gly Lys Ile Asp Gln Ala Pro Val
                 85                  90                  95

Leu Lys Ala Ala Ile Glu Gln Arg Trp Gly Ser Phe Asp Lys Phe Lys
                100                 105                 110

Asp Ala Phe Asn Thr Thr Leu Leu Gly Ile Gln Gly Ser Gly Trp Gly
            115                 120                 125

Trp Leu Val Thr Asp Gly Pro Lys Gly Lys Leu Asp Ile Thr Thr Thr
        130                 135                 140

His Asp Gln Asp Pro Val Thr Gly Ala Ala Pro Val Phe Gly Val Asp
145                 150                 155                 160

Met Trp Glu His Ala Tyr Tyr Leu Gln Tyr Leu Asn Asp Lys Ala Ser
```

```
                165                 170                 175
Tyr Ala Lys Gly Ile Trp Asn Val Ile Asn Trp Ala Glu Ala Glu Asn
            180                 185                 190

Arg Tyr Ile Ala Gly Asp Lys Gly His Pro Phe Met Lys Leu
        195                 200                 205
```

<210> SEQ ID NO 3
<211> LENGTH: 861
<212> TYPE: DNA
<213> ORGANISM: Artificial Sequence
<220> FEATURE:
<223> OTHER INFORMATION: Description of Artificial Sequence: recombinant
      allergen rAsp f4

<400> SEQUENCE: 3

```
ggcgaggtcg gcgacactgt ctacgctact ataaacggtg tcctcgtctc gtggatcaac      60
gagtggtccg gcgaggctaa gacctccgac gctcccgtct ctcaggctac tcccgtcagc     120
aacgctgtgg ctgccgccgc cgccgcttct actccggagc ccagctcttc ccactccgac     180
agttcttcat cctccggcgt ctccgccgac tggaccaaca cccctgccga aggcgagtac     240
tgcactgacg gcttcggtgg caggaccgaa cccagcggct ccggtatctt ctacaagggc     300
aacgttggta accctggggg cagcaacatc atcgaggtct cccccgagaa cgccaagaag     360
tacaagcacg tcgctcagtt tgttggcagc gacactgacc cctggaccgt tgtcttctgg     420
aacaagatcg gccccgatgg tggccttact ggctggtacg gtaactccgc tctgaccctc     480
cacctcgagg ccggtgagac caagtacgtg gcattcgacg agaactccca gggtgcctgg     540
ggcgccgcaa agggcgacga gctgcccaag gaccagtttg gtgggtactc ttgcacctgg     600
ggtgagttcg actttgacag caaaatcaac acggctggt ctggctggga cgtgtccgcc     660
attcaggccg agaatgccca ccatgaggtc cagggtatga agatctgcaa tcacgccggc     720
gagctctgct ccatcatctc ccacggtctt tccaaggtca ttgacgccta cactgctgat     780
ctggccggtg tcgatggcat tggtggcaag gtcgtccctg ccctacccg tctggtcgtc     840 aacctcgact acaaggagta g                                                861
```

<210> SEQ ID NO 4
<211> LENGTH: 286
<212> TYPE: PRT
<213> ORGANISM: Artificial Sequence
<220> FEATURE:
<223> OTHER INFORMATION: Description of Artificial Sequence: recombinant
      allergen rAsp f4

<400> SEQUENCE: 4

```
Gly Glu Val Gly Asp Thr Val Tyr Ala Thr Ile Asn Gly Val Leu Val
  1               5                  10                  15

Ser Trp Ile Asn Glu Trp Ser Gly Glu Ala Lys Thr Ser Asp Ala Pro
             20                  25                  30

Val Ser Gln Ala Thr Pro Val Ser Asn Ala Val Ala Ala Ala Ala Ala
         35                  40                  45

Ala Ser Thr Pro Glu Pro Ser Ser His Ser Asp Ser Ser Ser Ser Ser
     50                  55                  60

Ser Gly Val Ser Ala Asp Trp Thr Asn Thr Pro Ala Glu Gly Glu Tyr
 65                  70                  75                  80

Cys Thr Asp Gly Phe Gly Gly Arg Thr Glu Pro Ser Gly Ser Gly Ile
                 85                  90                  95

Phe Tyr Lys Gly Asn Val Gly Lys Pro Trp Gly Ser Asn Ile Ile Glu
```

```
              100              105              110
Val Ser Pro Glu Asn Ala Lys Lys Tyr Lys His Val Ala Gln Phe Val
            115              120              125
Gly Ser Asp Thr Asp Pro Trp Thr Val Val Phe Trp Asn Lys Ile Gly
    130              135              140
Pro Asp Gly Gly Leu Thr Gly Trp Tyr Gly Asn Ser Ala Leu Thr Leu
145              150              155              160
His Leu Glu Ala Gly Glu Thr Lys Tyr Val Ala Phe Asp Glu Asn Ser
                165              170              175
Gln Gly Ala Trp Gly Ala Ala Lys Gly Asp Glu Leu Pro Lys Asp Gln
            180              185              190
Phe Gly Gly Tyr Ser Cys Thr Trp Gly Glu Phe Asp Phe Asp Ser Lys
        195              200              205
Ile Asn His Gly Trp Ser Gly Trp Asp Val Ser Ala Ile Gln Ala Glu
    210              215              220
Asn Ala His His Glu Val Gln Gly Met Lys Ile Cys Asn His Ala Gly
225              230              235              240
Glu Leu Cys Ser Ile Ile Ser His Gly Leu Ser Lys Val Ile Asp Ala
                245              250              255
Tyr Thr Ala Asp Leu Ala Gly Val Asp Gly Ile Gly Gly Lys Val Val
            260              265              270
Pro Gly Pro Thr Arg Leu Val Val Asn Leu Asp Tyr Lys Glu
        275              280              285

<210> SEQ ID NO 5
<211> LENGTH: 336
<212> TYPE: DNA
<213> ORGANISM: Artificial Sequence
<220> FEATURE:
<223> OTHER INFORMATION: Description of Artificial Sequence: recombinant
      allergen rAsp f8

<400> SEQUENCE: 5
atgaagtacc tcgcagcttt cctcctcctc gcccttgctg caacacctc cccgtcctct      60 gaggatgtca aggccgtcct ctcttccgtt ggcattgatg ccgatgagga gcgcctgaac    120
aagctcattg ctgagctcga gggcaaggac ctccaggagc tcattgccga gggttccacc    180
aagctcgctt ccgttccctc cggtggtgct gccgccgctg ctcctgccgc tgccggtgcc    240
gctgccggtg gtgctgctgc tcctgccgct aaggagaaga tgaggagga gaaggaggag    300 tccgacgagg acatgggctt cggtctcttc gactaa                             336

<210> SEQ ID NO 6
<211> LENGTH: 111
<212> TYPE: PRT
<213> ORGANISM: Artificial Sequence
<220> FEATURE:
<223> OTHER INFORMATION: Description of Artificial Sequence: recombinant
      allergen rAsp f8

<400> SEQUENCE: 6

Met Lys Tyr Leu Ala Ala Phe Leu Leu Leu Ala Leu Ala Gly Asn Thr
  1               5                  10                  15
Ser Pro Ser Ser Glu Asp Val Lys Ala Val Leu Ser Ser Val Gly Ile
            20                  25                  30
Asp Ala Asp Glu Glu Arg Leu Asn Lys Leu Ile Ala Glu Leu Glu Gly
        35                  40                  45
```

```
Lys Asp Leu Gln Glu Leu Ile Ala Glu Gly Ser Thr Lys Leu Ala Ser
    50                  55                  60

Val Pro Ser Gly Gly Ala Ala Ala Ala Pro Ala Ala Ala Gly Ala
65              70                  75                  80

Ala Ala Gly Gly Ala Ala Ala Pro Ala Ala Lys Glu Lys Asn Glu Glu
                85                  90                  95

Glu Lys Glu Glu Ser Asp Glu Asp Met Gly Phe Gly Leu Phe Asp
            100                 105                 110

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: residue for
      attachment to C-terminus

<400> SEQUENCE: 7

Val Glu His His His His His His
 1               5

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: residue for
      attachment to N-terminal end

<400> SEQUENCE: 8

Met Arg Gly Ser His His His His His His Met
 1               5                  10
```

METHODS FOR DIAGNOSIS OF ALLERGIC BRONCHOPULMONARY ASPERGILLOSIS

TECHNICAL FIELD

The present invention relates to methods for the diagnosis of allergic bronchopulmonary aspergillosis (ABPA) and recombinant allergens to be used in the methods. During the priority year the recombinant allergen that in the priority application was called rAsp f2 has officially been named rAsp f6. The official name is used in this text.

TECHNICAL BACKGROUND

Allergic bronchopulmonary aspergillosis (ABPA). Allergic bronchopulmonary aspergillosis is the most severe allergic complication caused by Aspergillus species, mainly A. fumigatus. ABPA is the result of hypersensitivity to Aspergillus-antigens mainly in patients suffering from long-standing atopic asthma (8–12) or cystic fibrosis (16–19). Although originally considered as a rare disease (13), ABPA is currently recognized with much greater frequency. ABPA with varied clinical presentations has been reported to occur in about 15% of the asthmatic patients sensitized to A. fumigatus (14,15), while in patients with cystic fibrosis the reported incidence varies from 10 to 35% (16,17). ABPA has been described as an immune disease that ranges from asthma to fatal destructive lung disease with defined clinical, serological, radiological and pathological features (8,18–22). Because of its severity ABPA should be ruled out in patients with chronic asthma or cystic fibrosis exhibiting immediate cutaneous reactivity to A. fumigatus (8). The diagnostic criteria for ABPA are asthma or cystic fibrosis, history of roentgenographic infiltrates (in most cases), immediate cutaneous reactivity to A. fumigatus extracts, elevated total serum IgE, precipitating antibodies to A. fumigatus, peripheral blood eosinophilia, elevated specific serum IgE and IgG to A. fumigatus as compared to sera from patients with asthma and cutaneous reactivity to Aspergillus, but without ABPA, and proximal (central) bronchiectasis with normal tapering of distal bronchi (23–25). In cases where all criteria are present, diagnosis is readily made (26). However, all of the eight criteria are rarely present at the same time even in classic ABPA-patients with central bronchiectasis. With exception of bronchiectasis and to some extent elevated specific serum IgE and IgG to A. fumigatus, none of the diagnostic criteria are specific for ABPA (26). Furthermore, pulmonary infiltrates and central bronchiectasis are commonly detected in patients suffering from cystic fibrosis also in the absence of sensitization to A. fumigatus, which makes a diagnosis of ABPA in patients with cystic fibrosis even more difficult (16). Therefore, serologic identification of ABPA has a greater diagnostic potential, but is, however, hampered by the lack of standardized, reliable fungal extracts (5,7,27–29).

Aspergillus fumigatus antigens. The major problem in the immunodiagnosis of diseases related to A. fumigatus stems from the antigenic complexity of the fungus. Antigen/allergen extracts of A. fumigatus contain hundreds of different proteins (6,30,31), of which a limited subset are able to let bind human serum IgE (6,32,33,35). The fungus has been reported to produce more than 40 IgE-binding components which generate complex IgE-binding patterns when extracts are examined by Western blot analysis using sera from allergic individuals (32,33). To make the picture even more complicated, serum IgE from different patients recognize highly variable patterns of fungal proteins (6,36). In the case of patients suffering from ABPA, depending on the stage of the disease, different allergenic "fingerprints" may be obtained with serum of the same patient taken at different times, even if fungal extract from the same batch is used (36,37).

It has been suggested to use purified native allergenic components instead of crude allergen extracts for diagnosing ABPA (79). Recombinant A. fumigatus allergens with connections to ABPA have been described earlier (71,83).

The inventors are named authors in a number of articles about recombinant allergens from A. fumigatus (cloning and expression: 39,43,49,51,52,82, and diagnostic use: 59,66, 32,71,76,81).

Result of International-Type Search During the Priority Year.

The references 66, 79 and 84 have been categorised as being of particular relevance.

Banerjee et al., (84) describes antigens that cannot be intracellular. The described antigens are shown to react with sera of patients with ABPA, but there are no data suggesting that the antigens will not react with sera of A. fumigatus-sensitised patients not having ABPA.

Moser et al (66) and Little et al., (79) describe secreted proteins/antigens that do not allow for differential diagnosis of ABPA because they frequently reacts with sera of A. fumigatus-sensitised patients without ABPA and sera of ABPA patients.

THE OBJECTIVES OF THE INVENTION

The main objective of the invention is to provide improved methods for diagnosis of ABPA.

One subobjective is to provide in vitro diagnostic methods that have the sufficient specificity and sensitivity for diagnosis of ABPA.

A second subobjective is to provide well-defined allergen preparations that can be used for the diagnosis of ABPA both in vitro and in vivo, including immunoassay and skin reactivity measurement methods, respectively.

THE INVENTION

The first major aspect of the invention is a method for diagnosis of allergic bronchopulmonary aspergillosis (ABPA). This aspect is characterised in using as a reagent an ABPA-related recombinant allergen, i.e. a recombinant allergen carrying an epitope against which antibodies of various Ig classes/subclasses, such as of the IgE class or total IgG or IgG subclasses (IgG1, IgG2, IgG3 and IgG4) can be detected so that an ABPA condition in a patient can be differentiated from allergic sensitization to A. fumigatus, which is particularly useful in patients suffering from cystic fibrosis.

The concept of ABPA-related recombinant allergens includes any recombinant allergen, irrespective of origin, having the above-mentioned antibody binding feature permitting the differential diagnosis indicated. It encompasses in particular ABPA-related recombinant allergens derived from A. fumigatus and their ABPA-related fragments. For ABPA-related recombinant allergens cloned from A. fumigatus, the concept encompasses ABPA-related allergens and fragments derived from other sources, having one or more ABPA epitopes in common with an ABPA-related allergen from A. fumigatus. At the priority, date rAsp f4 and rAsp f6 and their fragments, as defined above, were considered to be the most useful ABPA-related allergens. Various derivatized forms retaining the ability to bind antibodies, as defined for ABPA-related recombinant allergens, are also included.

Various subaspects include in vitro and in vivo testing protocols as described below.

The second major aspect of the invention is novel ABPA-related recombinant allergens binding to human IgE present in ABPA patients and useful in the first aspect of the invention.

Various subaspects of this second major aspect of the invention are apparent from the below and encompasses derivatized forms including but not limited to underivatized, insolubilized and labelled ABPA-related allergens. Another aspect of the invention is the use of ABPA-related allergens for hyposensitization treatment as done for other allergens.
Cloning of Allergens from *Aspergillus fumigatus*.

The cloning strategy utilized phagemid pcomb3 (47) and the ability of the leucine zipper proteins Jun and Fos to associate with each other (74,48,74,75).

A modified gIII product, obtained by fusing the DNA encoding the jun leucine zipper flanked by cysteine residues, N-terminal to the viral coat protein was expressed from a LacZ promotor and secreted into the periplasmic space of *E. coli* by a pelB leader peptide, thereby being structurally incorporated into phage particles during infection with helper phage (49). Using a second LacZ promotor of the phagemid, the fos leucine zipper domain, flanked by cysteine residues, co-expressed as N-terminal fusion peptide to cDNA protein products of *A. fumigatus*, was secreted into the 4: periplasmic space of *E. coli* using the pelB leader peptide (50). Through Jun-Fos heterodimerization and disulfide bond formation, the gIII-Jun fusion protein incorporated into phage particles provides a covalent link to phage surface for random recombinant cDNA products with the Fos leucine zipper attached N-terminally (48,49). The phagemid pJuFo which contains the described elements (49,51,52), allows expression and display of cDNA libraries, in this case encoding shot-gun 19 cloned *A. fumigatus* peptides/proteins, on phage surface and application of the powerful screening technology based on biopanning procedures used for other filamentous phage systems (46,47). The key of success in cDNA cloning from libraries displayed on phage surface lies in the screening strategy used. The most important factor to be considered is that the ligand used to select phage should be tagged or immobilized in a way allowing the ligand to retain its native conformation (46). It must be taken into account that proteins, when directly immobilized to a solid phase by hydrophobic interaction, may lose biological activity due to alterations in the three-dimensional structure (54,55). In general the known or expected characteristics of the ligand will dictate the procedure used for ligand immobilization. For the isolation of allergens recognized by serum antibodies, the use of capture antibodies has proven to be very effective for different reasons. First, monoclonal antibodies raized against the immunoglobulin ε constant domains Cβ2, Cβ3 or Cβ4 do not interfere with the antigen binding site of the antibody. Second, a surface coated with such anti-IgE antibodies will be able to immobilize selectively IgE antibodies from serum of allergic patients. Therefore, after washing away interacting and cross-reacting serum antibodies of other isotypes together with all other serum components, a specific surface able to adsorb only phage displaying IgE binding molecules will be obtained (51–53).

The application of pJuFo to display cDNA products and select phages from a library constructed using mRNA from *A. fumigatus* (39,51,52) yielded a wide variety of phage clones able to bind IgE antibodies from sera of patients sensitized to *A. fumigatus* (table 1).

Compared with screening of λ-libraries immobilized on solid phase supports, the screening procedure for cDNA libraries displayed on the surface of filamentous phage has several advantages. Capturing serum IgE with an immobilized anti-IgE antibody generates a homogenous surface with immobilized IgE which does not become denatured (56,57) and therefore retain the full antigen binding capacity. The most important advantage results from the fact, that the phage library is kept in a liquid phase, where only phage with affinity to the ligand are retained on the solid phase after washing (47,53). Desorbed phage can be used to infect *E. coli* in order to amplify phage with affinity for the ligand. Therefore, successive rounds of phage growth and selection allow enrichment of phage displaying proteins with affinity for the ligand (table 3). After selection of candidate phage clones displaying proteins with IgE binding properties, phage particles produced from 10 ml culture can be precipitated (47) and samples of 1010–1013 phage particles of each candidate clone analysed by SDS-PAGE under reducing conditions, followed by transfer to nitrocellulose membranes (49,51). After blocking in order to saturate free binding sites on the nitro-cellulose sheet, membranes are incubated with patient serum diluted 1:10 as "first antibody" and mouse anti-human IgE mAb as second antibody can be used to visualize binding of IgE to the cDNA product originally present on the phage surface. Western blots can easily be developed using non-radioactive systems and horse-radish-peroxidase-conjugated goat-anti mouse Ig as detection system. The apparent molecular mass of the IgE-binding proteins enriched from an *A. fumigatus* cDNA library displayed on phage surface was in the range of 10 to more than 50 kDa. Nucleotide sequence determination (58) of some cDNA-inserts differing in size and restriction pattern revealed that they encode different proteins as deduced from the open reading frames.

Production of Recombinant Allergens in *E. coli*.

Illustrative examples of production methods will now be given for two ABPA-related recombinant allergens cloned from *A. fumigatus*, designated rAsp f4 and rAsp f6.

rAsp f6: DNA encompassing the coding sequence of rAsp f6 was cloned into an expression vector under the transcriptional control of the T7 promoter (78). The construct was designed in such a way that one methionine residue was added at N-terminal end of the allergen amino acid sequence, while at the C-terminus the eight-residue stretch -VEHHHHHH (SEQ ID NO:7) added, of which the six consecutive histidine residues serve as an affinity tag for metal-chelate affinity chromatography (61). After sequence confirmation, the construct was transferred to *E. coli* BL21 [pT7POL23] (77), in which synthesis of the T7 RNA polymerase can be induced by raising the temperature of the growing culture to above 37° C. To produce rAsp f66, 1 liter of LB medium containing an appropriate complement of antibiotics was inoculated with 1 ml of an overnight starter culture grown at 30° C. After approximately 3 hrs of growth at 30° C., at an $OD_{600}$ of 0.7, the temperature of the culture was shifted to 42° C. in order to induce expression. After 4 hrs of of incubation at inducing temperature, cells were harvested by centrifugation and resuspended in 50 ml of ice-cold 20 mM Tris-HCl pH 8.0 containing 0.5 M NaCl and 5 mM imidazol (resuspension buffer). The cells were disrupted by sonication and insoluble debris removed by centrifugation. The supernatant, containing the overexpressed allergen, was passed through a 0.22 μm filter to remove remaining particulate material and loaded onto an assembly of two serially connected 5 ml HiTrap Chelating columns (Pharmacia Biotech AB, Uppsala, Sweden) previously charged with $Ni^{2+}$ and equilibrated with resuspension buffer. The column assembly was washed first with 50 ml of resuspension buffer, then with 50 ml of resuspension buffer supplemented with Imidazol to 60 mM. To elute rAsp f6, a 30 ml linear gradient of 60–500 mM imidazol in 20 mM Tris-HCl pH8.0/0.5 M NaCl was applied while 1 ml fractions were collected and analysed by SDS-PAGE. Fractions containing rAsp f6 were pooled and subjected to gel filtration through a Superdex 200 column (Pharmacia Biotech AB, Uppsala, Sweden) equilibrated and eluted with 0.15 M NaCl. Fractions containing rAsp f6 were pooled and concentrated using an Amicon cell fitted with a YM5 membrane. Final yield of purified rAsp f6 from one liter of bacterial culture was 23 mg.

rAsp f4: DNA encompassing the coding sequence of rAsp f4 was cloned into an expression vector under the transcriptional control of the T7 promoter (78). The construct was designed in such a way that the 11-residue stretch MRGSHHHHHHM-(SEQ ID no:8) was added to N-terminal end of the allergen amino acid sequence, of which the six consecutive histidine residues serve as an affinity tag for metal-chelate affinity chromatography (61). No amino acid addition was made at the C-terminal end of the protein. After sequence confirmation, construct was transferred to $E.$ $coli$ BL21[pT7POL23] (77), in which synthesis of the T7 RNA polymerase can be induced by raising the temperature of the growing culture to above 37° C. To produce rAsp f4, 1 liter of LB medium containing an appropriate complement of antibiotics was inoculated with 1 ml of an overnight starter culture grown at 30° C. After approximately 3 hrs of growth at 30° C., at an $OD_{600}$ of 0.7, the temperature of the culture was shifted to 42° C. in order to induce expression. After 4 hrs of of incubation at inducing temperature, cells were harvested by centrifugation and resuspended in 50 ml of ice-cold 20 mM Tris-HCl pH 8.0 containing 0.5 M NaCl. The cells were disrupted by sonication and insoluble material including rAsp f4 protein was collected by centrifugation. The insoluble material was washed twice by resuspension in 20 mM Tris-HCl pH 8.0 containing 2 M Urea, 0.5 M NaCl and 2% Triton X-100, followed by centrifugation. Partially purified rAsp f4-containing inclusion bodies were extracted for 45 minutes at room temperature in 70 ml of 20 mM Tris-HCl pH8.0 containing 6 M guanidinium hydrochloride, 0.5 M NaCl, 5 mM Imidazol and 1 mM 2-mercaptoethanol (extraction buffer). The extract was clarified by centrifugation and remaining particulate material removed by passage through a 0.22 μm filter. The clarified extract, containing the overexpressed allergen, was loaded onto an assembly of two serially connected 5 ml HiTrap Chelating columns (Pharmacia Biotech AB, Uppsala, Sweden) previously charged with $Ni^{2+}$ and equilibrated with extraction buffer lacking 2-mercaptoethanol. The column assembly was washed first with 50 ml of extraction buffer, then with 50 ml of 6 M urea in 20 mM Tris-HCl pH 8.0, 0.5 M NaCl, 20 mM Imidazol and 1 mM 2-mercaptoethanol (urea wash buffer). In order to renature the immobilized rAsp f4, a 960 ml linear gradient was applied, from urea wash buffer to 20 mM Tris-HCl pH8.0 containing 0.5 M NaCl, 20 mM Imidazol and 1 mM 2-mercaptoethanol (renaturation buffer). To elute rAsp f4, a 30 ml gradient of 20–1000 mM imidazol in renaturation buffer was applied while 1 ml fractions were collected and analysed by SDS-PAGE. Fractions containing rAsp f4 were pooled and subjected to gel filtration through a Superdex 75 column (Pharmacia Biotech AB, Uppsala, Sweden) equilibrated and eluted with 0.15 M NaCl. Fractions containing rAsp f4 were pooled and concentrated using an Amicon cell fitted with a YM10 membrane. Final yield of purified rAsp f4 from one liter of bacterial culture was 34 mg.

Production has also been carried out with the vector described by Hochli et al (60–63).

Analysis of cDNL inserts

Only inserts coding for peptides/proteins relevant for the diagnosis of ABPA will be discussed.

rAsp f6 (SEQ ID NO 1). A clone containing an insert of 751 base pairs with an open reading frame of 624 base pairs revealed a strong homology with nucleotide sequences encoding superoxide dismutases. The 3'-noncoding region had a polyadenylated tail of 24 base pairs. The deduced amino acid sequence of this cDNA clone (SEQ ID NO 1) was homologous to manganese SOD, showing the highest sequence identity of 48–52% to the human, fruit fly, gum tree, yeast, $E.$ $coli$, and $Mycobacterium$ $leprae$ enzymes. Apparently the $A.$ $fumigatus$ MnSOD displays a similar high degree of sequence identiy to MnSODs from a wide variety of phylogenetically distant organisms (43). Multiple sequence alignment shows that the $A.$ $fumigatus$ MnSOD (rAsp f6) shares high homology with human MnSOD (51.8% identity, 67.2% homology). IgE raised against $A.$ $fumigatus$ MnSOD is detected predominantly in sera of patients suffering from ABPA. Therefore MnSOD could be a candidate for a serologic differential discrimination between ABPA and $A.$ $fumigatus$ allergy (see below). Notably, both recombinant $A.$ $fumigatus$ and human MnSOD induce proliferation in peripheral blood mononuclear cells of $A.$ $fumigatus$ allergic subjects with detectable levels of specific IgE to $A.$ $fumigatus$ MnSOD. Moreover, both the fungal and human recombinant MnSODs elicited Type I skin reactions in individuals sensitized to the fungal enzyme, providing evidence for auto-reactivity to human MnSOD in allergic individuals sensitized to the environmental $A.$ $fumigatus$ allergen (43).

rAsp f4 (SEQ ID NO 2). This was the second recombinant ABPA-related allergen discovered in our screening system. The clone contained an isert of 1103 base pairs with an open reading frame of 858 base pairs. Its deduced amino acid sequence does not share significant homology to any known protein. The gene product encoded by the used cDNA was only characterized by the function for which it was selected: IgE binding.

In Vivo Tests Utilizing Recombinant Allergens.

These are mainly illustrated by skin prick tests in which a small amount of a solution of an allergen is inserted into the dermis of an individual whereupon a wheal reaction occurs around the place for administration.

One protocol for skin prick tests of the invention implied that a recombinant allergen was dissolved in 0.9% physiological saline as a diluent at an end concentration of 100 μg/ml. 20 μl of these solutions were placed on the patient's forearms. Thereafter the skin was pricked with a sterile needle, which was entered into the epidermis at a degree angle and lifted up to elevate a small portion of the epidermis (38). The needle was discarded after the application of each solution to avoid contamination. The test sites were placed 3 to 4 cm apart to avoid false positive results.

For intradermal tests, an allergen solution (100 μg/ml) were diluted at serial 10-fold dilutions and applied at concentrations starting from 10–4 μg/ml to 10 μg/ml. For testing the solutions (100 μl) were injected on the patients' backs starting from the solution with lowest concentration resulting in a size of the wheal of half the size of the skin reaction induced by the histamine control. The test sites were placed 5 to 8 cm apart to avoid false-positive results. Histamine dihydrochloride was used as a positive control at concentrations of 0.1% in skin prick tests or 0.01% in intradermal tests, respectively. Physiological 0.9% salime was used as a negative control. The reactions were recorded after 15 minutes by measuring the maximal longitudal and transversal diameter of the wheal and evaluated as described (66).

The Use of Recombinant $A.$ $fumigatus$ Allergens for In Vitro Diagnostics.

The binding of recombinant $A.$ $fumigatus$ allergens to antibodies may be used in immunoassays for measuring allergen/antigen specific antibodies of various classes (IgA, IgG, IgD, IgE and IgM), including specific subclasses thereof, for instance in connection with diagnoses of allergy and ABPA. Among IgG subclasses may be mentioned IgG1, IgG2, IgG3 and IgG4. The methodology for the assays is the same as that used in the prior art for conventional antigens/allergens. Suitable immunoassay protocols thus contemplate formation of a ternary immune complex:

[allergen]-[anti-allergen antibody]-[anti-antibody]
where allergen and anti-antibody are added reagents and anti-allergen antibody derives from the sample to be assayed. The complex is formed in an insoluble or insolubilizable form. Insoluble forms are accomplished by having either the allergen or the anti-antibody bound to a solid phase before, after or during formation of the complex. Well known solid phases in the field are walls of tubes and wells, particulate and monolithic more or less porous materials used as adsorbents in chromatography and heterogeneous imunoassays etc. In order to measure the amount of complex, either the allergen or the anti-antibody is labelled with an analytically detectable group, with the provision that the reagent linked to a solid phase or causing post-insolubilization is not labelled. Well known detectable groups are enzymes (ELISA), fluorophors, chromophors, chemiluminescent groups, radioactive isotopes, metal atoms, biotin, haptens etc. In order to measure class/subclass specific antigen/allergen specific antibodies the anti-antibody has to be class/subclass specific. Normally this type of immunoassay is run with sequential incubation, i.e.

step 1: sample with allergen followed by step 2: incubation of the complex formed in step 1, i.e.

[allergen]-[anti-allergen antibody] with anti-antibody
or vice versa. In case the reagent used in step 1 is bound to a solid phase, separation and washing after each step should be carried out in order to remove unspecific interference.

For ABPA diagnosis, IgE and certain IgG subclasses are the most relevant Igs to measure. It is believed that the recombinant allergens to be used should be derived from A fumigatus proteins not being exposed on the cell surface or secreted. This may indicate that the most relevant *A. fumigatus* allergens relevant for ABPA may be cell-bound, for instance as intracellular peptides/proteins.

Relevant antibodies can be found in blood (including plasma and serum), saliva, cerebrospinal fluid (CSF), bronchioalveolar fluid, tear drops (lacrymal fluid) etc.

The In Vitro Test Protocols Used and Results.

The binding of IgE antibodies (and other isotypes) to recombinant allergens was assessed by an ELISA (39) using the same method for all allergens. Briefly, polystyrene microtiter plates were coated for 2 h at 37° C. with allergen protein (10 μg/ml in PBS, pH 8.0). The free sites were blocked with PBS, pH 7.4 containing 5% (w/v) non-fat dry milk powder (1 h, 37° C.). After washing, the plates were incubated with serially twofold-diluted sera in blocking buffer containing 5% Tween 20 (2 h, 37° C.). After washing, a second antibody of commercial source (66) or TN-142, a mouse monoclonal anti-human IgE antibody raised against the Cε2 domain (kindly supplied by Dr C. H. Heusser, Ciba-Geigy Ltd., Basel. Switzerland) were used to quantify the isotype-specific Ig-content of the sera. Isotype-specific Ig-binding to the allergens was detected with alkaline-phosphatase-conjugated goat anti-mouse IgG (66, 69). In absence of calibrated standards, a serum pool from two patients suffering from ABPA was used as an in house reference. Serum dilutions versus optical density were plotted in a log—log diagram and the linear titrable region used to convert the optical density values to arbitrary ELISA units (EU). Absorbence values from the reference serum pool were arbitrarily set as 100 EU/ml for all isotypes analysed (66,68). The antigen-specific ELISA allows reliable detection of serum antibodies. For the IgE-determinations using rAsp f6, the results have been validated using Pharmacia CAP System (Pharmacia & Upjohn, Diagnostics, Uppsala, Sweden) with the recombinant proteins as immobilized allergen.

For a large scale evaluation of the in vitro diagnostic value of recombinant *A. fumigatus* allergens, 54 sera from patients suffering from ABPA and from 35 allergic asthmatics with *A. fumigatus* sensitization but without ABPA as deduced from the clinical parameters were selected. All patients had asthma and met the guidelines for the diagnosis and management of asthma (70). As negative control, sera from 10 allergic asthmatics without *A. fumigatus* sensitization and from 10 healthy individuals without history of atopy were used. In contrast to sera from sensitized individuals, the serum samples of the 20 control individuals showed IgE values below the background for all recombinant allergens, demonstrating that the IgE detection system is related to specific sensitization to *A. fumigatus*. The results of the IgE determinations obtained with sera of *A. fumigatus* allergic asthmatics with or without ABPA for the relevant recombinant allergens so far discovered (rAsp f4 and rAsp f6) will be discussed below.

The serological investigations rAsp f4 and rAsp f6 show a completely different picture compared to that obtained with other recombinant *A. fumigatus* allergens. Specific IgE against rAsp f4 and rAsp f6 was not detectable in the 35 sera from allergic asthmatics sensitized to the fungus. In contrast, the 54 sera from ABPA-patients recognized rAsp f4 and rAsp f6 at a frequency of 54% and 78%, respectively, (table 3), whereas 49 sera recognized at least one of the allergens. Therefore, serologic diagnosis of ABPA with the two allergens has a specificity of 100% and a sensitivity >90% (table 4). The MNSOD (rAsp f6), a protein with a known biochemical function, represents a strictly intracellular enzyme. The biobiological function of Asp f4 remains unknown; however, preliminary experiments to locate the protein using monoclonal antibodies raised against Asp f4 indicate that the protein is not secreted by the fungus. Therefore both proteins are unlikely to be present in free form as aeroallergens, which may explain the lack of specific IgE against these allergens in allergic asthmatics sensitized to *A. fumigatus*. In contrast, patients suffering from ABPA have or have had the fungus growing in the lung (8,12) and as a result of disintegration of fungal cells by host defence mechanisms, become exposed also to non-secreted proteins (3). One of the host defence mechanisms against fungal infections consists of the damage of hyphae and phagocytosis mediated by polymorphonuclear cells (2,3,4). Development of a cell-mediated immune response to a fungus is thought to require antigen-presenting cells to process and present fungal antigens to T-lymphocytes (1). Therefore patients suffering from ABPA are able to mount an immune response also to intracellular proteins of *A. fumigatus* never seen by the immune system of *A. fumigatus*-allergic individuals, which are exposed only to secreted allergens and conidiae. The in vivo relevance of rAsp f4 and rAsp f6 has been assessed in skin tests involving representative numbers of patients with ABPA, *A. fumigatus* allergy and healthy controls (see below).

Diagnostic Value of Recombinant *A. fumigatus* Allergens for In Vivo Tests.

Regarding a potential discrimination between ABPA and allergic sensitization, the most significant findings of the serologic investigations, involving subjects with asthma and concomitant sensitization to *A. fumigatus* were elevated levels of specific serum IgE to rAsp f4 and rAsp f6 in patients suffering from ABPA. As indicated in table 3, rAsp f4- and rAsp f6-specific IgE, as measured by ELISA, reached values of 54±160 ELISA Units/ml and 47±66 ELISA Units/ml in sera of asthmatic patients with ABPA. In contrast, specific IgE antibodies to these two allergens were virtually absent in sera of asthmatic patients sensitized to *A. fumigatus* without evidence for ABPA, as well as in sera of control individuals (table 3). Based on these results, rAsp f4 and rAsp f6 could serve as reagents for the development of an ABPA-specific assay based on circulating allergen-specific IgE antibodies. It was therefore of interest to assess the allergenicity of these proteins in vivo. To demonstrate the ability of rAsp f4 and rAsp f6 to elicit mediator release in vivo, an intradermal skin provocation study was carried out involving 12 asthmatic patients with ABPA, 12 allergic asthmatics sensitized to *A. fumigatus* without ABPA and 5 healthy controls. Selection of patients and diagnosis of sensitization to *A. fumigatus* were based on clinical history, RAST and skin reactivity to *A. fumigatus* extracts as described (59,66). All patients had asthma and met the guidelines for the diagnosis and management of asthma (70). At the time of the study all subjects had stable bronchial asthma, no evidence for chest infections and received no anti-histamine medication. The five healthy control individuals had no history of allergy or asthma and had normal serum levels of total IgE. The diagnosis of ABPA was based on a minimum of six of the eight criteria proposed by Rosenberg et al (23) and Patterson et al (24). Four ABPA patients (table 5) and one patient with allergic asthma (table 5) were treated with low doses of oral corticosteroids (5–10 mg/day). An ethical approval for skin testing human subjects with recombinant allergens was obtained from the responsible committee before starting the study. A full explanation of the procedure was given to all individuals before testing and subsequently a written consent was obtained. The main characteristics of the subjects participating in the study including age, sex, eosinophil count, total serum IgE, specific serum IgE to rAsp f4 and rAsp f6 and RAST to *A. fumigatus* are reported in table 5. All subjects showed a positive skin test response to intradermal histamine challenges (0.01%) and were non-reactive to 0.9% saline. The results (table 5) suggest a high specificity of rAsp f4 and rAsp f6 reactivity for patients suffering from ABPA. In fact, only this group of patients showed relevant amounts of specific IgE against rAsp f4 and rAsp f6 (Table 3 and 4). As expected, only individuals showing detectable amounts of allergen-specific IgE in serum reacted to skin challenges with rAsp f4 and rAsp f6. These results clearly show that a highly specific diagnosis of ABPA based on recombinant allergens is feasible. However, although rAsp f4- and rAsp f6-based serology and skin tests show a high specificity for ABPA in the absence of atopic dermatitis, the sensitivity of the diagnosis reaches only about 90% (table 4). Taking into account the the relatively low specificity of the diagnostic criteria for ABPA available to date, serological and skin tests with rAsp f4 and rAsp f6 represent a considerable improvement of the diagnosis of the disease. Moreover, the characteristics of both allergens, taken together with the observation that ABPA patients and *A. fumigatus* sensitized allergic asthmatics recognize different allergen in Western blot analysis, provide a rational for a further improvement of the diagnosis of ABPA. In a study reported by Borga (6), serum IgE-reactivity to *A. fumigatus* allergens in two groups of patients were compared, *A. fumigatus* sensitized allergies and ABPA patients. Sera of individuals suffering from A fumigatus allergy recognized at least thirty-five different IgE-binding components of the fungus, ranging between 14 and 118 kDa in size, of which four components (34, 39, 43 and 83 kDa) were uniquely detected by these sera. With sera from the ABPA group, thirty-nine different IgE-binding components ranging from 14 to 150 kDa were detected, of which eight components with molecular weights of 15, 19.5, 54, 56, 96, 110, 126 and 150 kDa were not recognized by IgE from the allergies. Therefore, from the total of 43 IgE-binding components detected, antibodies to 31 were found in both of the patient groups, 8 were specific for ABPA and 4 specific for non-ABPA-related sensitization to *A. fumigatus*.

The availability of the recombinant allergens described ill allow identification of *A. fumigatus*-allergic who lack sensitization to these cloned allergens. Sera from such subjects can subsequently be used to screen the *A. fumigatus* phage surface display library in order to isolate phage clones displaying additional allergens. The powerful screening procedure based on biopanning (45,47,51,52), together with a rational for the selection of the sera used to screen the phage library, will allow isolation of the additional allergens in a reasonable time. Production, characterization and evaluation of these allergens are likely to contribute to the further development specific diagnosic tools for both ABPA and *A. fumigatus*-related sensitization.

In order to use rAsp f6 as a specific allergen for the diagnosis of ABPA, atopic dermatitis has to be excluded. A high percentage of patients suffering from atopic dermatitis with a moderate RAST class to *A. fumigatus* shows high titres of rAsp f6-specific IgE in serum. Moreover, intradermal skin challenges with rAsp f66 in three patients suffering from atopic dermatitis clearly demonstrated that the allergen is able to provoke a strong in vivo mediator release in these patients. Notably the serologic investigation of 15 sera of patients suffering from atopic dermatitis does not show any specific IgE to the other recombinant *A. fumigatus* allergens available (76). The reason for the monovalent sensitization to Asp f2 in patients with atopic dermatitis is unknown. However, it is tempting to speculate that the specific IgE response against rAsp f6 could be due to production of IgE antibodies recognizing human superoxide dismutase in these individuals, which would result in a cross-reaction to the highly homologous fungal MnSOD (43). The availability of both the human and fungal recombinant MnSOD will allow a study of the role of these proteins in the pathophysiology of atopic dermatitis in more detail.

Serologic Discrimination Between Sensitization to *A. fumigatus* and ABPA in Patients with Cystic Fibrosis.

This study involved 37 patients with cystic fibrosis with routine assessment for cystic fibrosis and allergy, including skin prick testing (67,71). 15 were diagnosed as having ABPA according to the clinical and immunological criteria proposed by Laufer (16) and Nelson (25). 12 patients belonged to the group with documented sensitization to *A. fumigatus* according to RAST and routine skin prick test to *A. fumigatus* extracts 2 and 10 were assigned to the CF control group based on the lack of sensitization. to *A. fumigatus* (67). Patient characteristics including age, sex, RAST to *A. fumigatus* and total serum IgE are reported in table 6. Allergen specific IgE levels were determined for the allergens rAsp f1, rAsp f3, rAsp f4 and rAsp f6 in serum of each individual. rAsp f1 (43) and rAsp f3 (42) correspond to major allergens of *A. fumigatus* with a prevalence of sensitization of 69% and 76% among asthmatic patients with positive skin test to *A. fumigatus* extracts, whereas rAsp f4 snd rAsp f6 (43) are recognized only by sera of patients with ABPA. All four proteins have been demonstrated to be relevant allergens in vivo by skin challenges of asthmatic patients sensitized to *A. fumigatus*. The results of the serological investigation (table 9) show that the majority of the cystic fibrosis individuals sensitized to *A. fumigatus* are carry IgE to rAsp f1 and rAsp f3 (85% and 100%, respectively) and 85% to both allergens. Taken together rAsp f1 and rAsp f3 are sufficient to diagnose sensitzation to *A. fumigatus* in all of the investigated sera from cystic fibrosis patients. According to the current definition of allergens (41) rAsp f1 and rAsp f3 correspond to major allergens also for the group of cystic fibrosis. In the three subgroups of individuals analyzed, cystic fibrosis patients with *A. fumigatus* sensitization, with or without ABPA, and cystic fibrosis individuals without *A. fumigatus* sensitization, relevant levels of serum IgE against rAsp f4 and rAsp f6 were found only in sera of individuals with a clinical diagnosis of ABPA. In this group rAsp f6-specific IgE levels exceeding the cut off value (>5 U/ml) were detected in 10 of 15 patient sera, while relevant levels of rAsp f4-specific IgE (cut off value >7 EU/ml) were detected in 13 of the 15 patient sera. If we consider elevated levels of either rAsp f4- or rAsp f6-specific IgE sufficient to indicate ABPA, all patients were covered by the serological diagnosis, whereas 8 patients of 15 had elevated levels of IgE to both rAsp f6 and rAsp f4. Therefore allergen-specific serology with rAsp f4 and rAsp f6 could give a substantial contribution to a differential serological diagnosis of ABPA in patients suffering from cystic fibrosis and *A. fumigatus* sensitization.

TABLE 1

Typical enrichment of phage from a cDNA phage display library by biopanning. Phage displaying cDNA-products from an *A. fumigatus* expression library were applied to a single well of a microtitre plate coated with human serum IgE (51,52). After adsorption and extensive washing adherent phages were eluted and used to infect *E. coli* for a further round of phage growth and selection.

| Round of panning | Phage input a | Phage output b | Enrichment factor c | IgE-specific phage tested d |
|---|---|---|---|---|
| 1 | 1.8 × 1011 | 4.5 × 103 | 5.6 × 10−6 | 0/10 |
| 2 | 8.6 × 1010 | 2.4 × 104 | 5.6 × 10−5 | 0/10 |
| 3 | 9.3 × 1010 | 4.6 × 104 | 3.8 × 10−5 | 0/10 |
| 4 | 6.5 × 1010 | 1.1 × 105 | 1.9 × 10−4 | 1/10 |
| 5 | 1.8 × 1011 | 3.8 × 106 | 2.3 × 10−3 | 8/10 |
| 6 | 2.1 × 1011 | 8.4 × 106 | 4.0 × 10−3 | 10/10 |
| 7 | 9.4 × 1010 | 5.8 × 107 | 5.6 × 10−2 | 10/10 | a Number of phage applied to a single well of a microtitre plate.
b number of phage eluted from the well after washing.
c Percentage yield of phage from each round of panning (% yield = [No. of phage eluted × 100]/[No. of phage applied]).
d Single colonies from plates used to titrate phagemids were grown in liquid culture, phage induced and purified. Phage coated directly to microtitre plates were tested for IgE binding capacity by an IgE-specific ELISA (66). IgE-specific phage represents phage able to bind serum IgE/number of phage tested.

TABLE 2

Main characteristics of phages isolated from an *A. fumigatus* cDNA library displayed on a phage surface and subjected to selective enrichment using patient serum IgE as ligand.

| Phage No | Insert[a] length bp | Mw of the[b] protein (kDa) | Expression[c] mg/l culture | IgE-binding[d] frequency | Preliminary[e] designation | Skin Test[f] reactivity |
|---|---|---|---|---|---|---|
| 2 | 1103 | 40 | 36 | <50% | rAsp f4 | + |
| 7 | 854 | 10 | 65 | <50% | rAsp f7 | nt |
| 19 | 751 | 28 | 220 | <50% | rAsp f6 | + |
| 28 | 616 | 21 | 38 | <50% | rAsp f3 | + |
| 38 | 1123 | 33 | 25 | <50% | rAsp f9 | nt |
| 46 | 686 | 18 | 140 | <50% | rAsp f1/a[g] | + |
| 48 | 1270 | 42 | 45 | <50% | rAsp f5 | + |
| 51 | 978 | 34 | 29 | <50% | rAsp f10 | nt |

[a]Determined from the nucleotide sequences
[b]Estimated from polyacrylamide gels
[c]Produced as inclusion body protein after subcloning of the fragments into pDS76/RBSII, 6xHis (62). The yields represent mg of Ni2+-chelate affinity purified proteins per liter culture (60,61).
[d]Sera from 54 patients with ABPA and from 35 individuals sensitized to *A. fumigatus* were tested for the presence of specific IgE to the recombinant proteins. IgE-binding frequency was assigned to major (>50%) or minor (<50%) allergens (41).
[e]Nomenclature not officialized.
[f]Skin test reactivity determined as described (66), nt = not tested.
[g]This allergen has been previously described.

TABLE 3

Sensitization of asthmatic patients with ABPA or *A. fumigatus* allergy to recombinant allergens rAsp f4 and rAsp f6.

| Subject groups | rAsp f6 | rAsp f4 |
|---|---|---|
| ABPA (n = 54) | 54 ± 160 a | 47 ± 66 |
| sensitized | 30 (56%) b | 42 (78%) |
| Allergic (n = 35) | 1 ± 1 | 2 ± 3 |
| sensitized | 0 (0%) | 0 (0%) |
| ABPA + allergics (n = 89) | 33 ± 89 | 29 ± 56 |
| sensitized b | 30 (56%) | 42 (78%) |
| Healthy controls (n = 20) | <5 | <5 |
| sensitized | 0 (0%) | 0 (0%) | a Mean value of IgE-binding to the allergen + SD (ELISA Units/ml).
b Number and % of samples showing IgE s sensitized to the allergen above cut-off level (5 and 7 EU/ml for rAsp f4 and rAsp f4, respectively).

TABLE 4

Discrimination between ABPA and sensitization to *A. fumigatus* by rAsp f4 and rAsp f6 IgE-specific serology.

| | Number (%) individuals sensitized to allergen | | | |
|---|---|---|---|---|
| Subjects | rAsp f6 | rAsp f4 | rAsp f6/rAsp f4 | rAsp f6 + rAsp f4 |
| ABPA (n = 54) | 30 (56%) | 42 (78%) | 49 (91%) | 25 (46%) |
| *A. fumigatus* allergics (n = 35) | 0 (0%) | 0 (0%) | 0 (0%) | 0 (0%) |
| Controls (n = 20) | 0 (0%) | 0 (0%) | 0 (0%) | 0 (0%) |
| Specificity and sensitivity for recognition of sera from ABPA-patients | | | | |
| Specificity | 100% | 100% | 100% | 100% |
| Sensitivity | 56% | 78% | 91% | 47% |

TABLE 5

Principal characteristics of the subjects studied and skin reactivity to rAsp f4 and rAsp f6.

| Subject | age y | sex | Eos/ml ×10⁶ | Total IgE kU/l | RAST | Specific IgE to a rAsp f6 | rAsp f4 | Skin test to b rAsp f6 | rAsp f4 |
|---|---|---|---|---|---|---|---|---|---|
| ABPA ||||||||||
| 1 | 62 | f | 0.71 | 475 | 3 | 22 | 0 | ++ | - |
| 2 | 46 | m | 0.37 | 1508 | 4 | 177 | 48 | ++++ | +++ |
| 3 | 28 | m | 0.45 | 4576 | 5 | 346 | 18 | +++ | + |
| 4 | 59 | f | 0.35 | 10957 | 5 | 1 | 537 | - | ++ |
| 5 | 56 | m | 0.91 | 637 | 5 | 0 | 11 | - | ++ |
| 6 | 52 | m | 0.19 | 2476 | 5 | 45 | 46 | ++++ | ++ |
| 7 | 55 | f | 0.24 | 1779 | 5 | 86 | 33 | ++++ | ++ |
| 8 | 32 | m | 0.57 | 1472 | 4 | 0 | 82 | - | ++++ |
| 9 | 53 | m | 0.23 | nd c | nd | 1 | 1 | - | - |
| 10 | 62 | m | 0.15 | nd | nd | 0 | 18 | - | + |
| 11 | 60 | f | 0.08 | 629 | 4 | 0 | 47 | - | +++ |
| 12 | 43 | m | 0.53 | | | 29 | 8 | +++ | ++ |
| *A. fumigatus* allergy ||||||||||
| 1 | 32 | m | 0.08 | 4913 | 1 | 4 | 1 | - | - |
| 2 | 60 | m | 0.20 | 76 | 3 | 0 | 0 | - | - |
| 3 | 30 | f | 0.52 | 67 | 3 | 1 | 2 | - | - |
| 4 | 43 | f | 0.05 | 3328 | 5 | 0 | 0 | - | - |
| 5 | 49 | f | 0.75 | 354 | 3 | 2 | 0 | - | - |
| 6 | 34 | m | 0.19 | 354 | 2 | 0 | 0 | - | - |
| 7 | 46 | f | 0.68 | 494 | 3 | 0 | 1 | - | - |
| 8 | 59 | m | 0.53 | 116 | nd | 1 | 2 | - | - |
| 9 | 58 | m | 0.84 | >2000 | 3 | 1 | 1 | - | - |
| 10 | 57 | m | 0.05 | nd | nd | 0 | 1 | - | - |
| 11 | 35 | f | 0.41 | >2000 | 4 | 0 | 0 | - | - |
| 12 | 44 | f | 0.26 | 1759 | 2 | 1 | 2 | - | - |
| Healthy controls ||||||||||
| 1 | 44 | m | 0.18 | 148 | 0 | 0 | 0 | - | - |
| 2 | 33 | m | 0.40 | 25 | 0 | 1 | 0 | - | - |
| 3 | 30 | f | 0.16 | 39 | 0 | 0 | 0 | - | - |
| 4 | 34 | m | 0.43 | 18 | 0 | 0 | 0 | - | - |
| 5 | 41 | m | 0.26 | 61 | 0 | 0 | 1 | - | - | a Relative Elisa Units/ml
b Positive reaction to intradermal skin challenges with rAsp f6 and rAsp f4 at concentrations of 1 µg (+), 100 ng (++), 10 ng (+++), or 1 ng (+++).
c nd 0 not determined.

TABLE 6

Serologic investigations of patients with cystic fibrosis with or without sensitization to *A. fumigatus* extracts.

| Subject | age y | sex | Total IgE kU/l | RAST | Specific IgE to rAsp a f1 | f2 | f3 | f4 |
|---|---|---|---|---|---|---|---|---|
| 1 | 11 | f | 2398 | 4 | 1224 | 1 | 265 | 76 |
| 2 | 12 | f | 5226 | 4 | 233 | 5 | 867 | 35 |
| 3 | 7 | m | 3804 | 4 | 747 | 733 | 4027 | 405 |
| 4 | 17 | m | 5423 | 4 | 173 | 100 | 658 | 53 |
| 5 | 22 | f | 1532 | 4 | 65 | 5 | 502 | 44 |
| 6 | 15 | f | 1017 | 4 | 45 | 30 | 178 | 13 |
| 7 | 16 | m | nd b | 4 | 1439 | 381 | 749 | 422 |
| 8 | 28 | m | 2126 | 4 | 122 | 23 | 340 | 17 |
| 9 | 12 | m | 866 | nd | 1037 | 60 | 3511 | 524 |
| 10 | 16 | m | 945 | 4 | 402 | 5 | 1057 | 27 |
| 11 | 28 | m | 576 | 4 | 208 | 346 | 287 | 18 |
| 12 | 19 | m | 928 | 3 | 48 | 97 | 183 | 4 |
| 13 | 16 | m | nd | 3 | 195 | 55 | 145 | 29 |
| 14 | 14 | m | nd | nd | 81 | 3 | 128 | 43 |
| 15 | 27 | f | 491 | 4 | 115 | 118 | 1529 | 3 |
| *A. fumigatus* allergy |||||||||
| 1 | 12 | m | 435 | 4 | 63 | 5 | 453 | 2 |
| 2 | 30 | f | 554 | 4 | 45 | 5 | 21 | 2 |
| 3 | 24 | f | 323 | 4 | 2 | 1 | 1176 | 3 |
| 5 | 24 | m | 166 | 3 | 5 | 0 | 32 | 3 |
| 6 | 14 | f | 146 | 3 | 7 | 3 | 117 | 1 |
| 7 | 21 | m | 304 | 4 | 145 | 1 | 121 | 4 |
| 8 | 33 | m | 372 | 3 | 91 | 0 | 437 | 3 |
| 9 | 16 | f | 103 | 3 | 3 | 0 | 131 | 3 |
| 10 | 29 | f | 270 | 3 | 21 | 0 | 88 | 2 |
| 11 | 28 | m | 47 | 2 | 87 | 2 | 124 | 4 |
| 12 | 31 | m | 409 | 3 | 167 | 2 | 128 | 0 |
| Cystic fibrosis controls |||||||||
| 1 | 20 | f | 56 | 0 | 2 | 2 | 9 | 5 |
| 2 | 30 | m | 115 | 0 | 3 | 4 | 7 | 2 |
| 3 | 30 | m | nd | 0 | 5 | 0 | 3 | 2 |
| 4 | 26 | f | nd | 0 | 1 | 0 | 1 | 0 |
| 5 | 31 | m | 40 | 0 | 4 | 0 | 3 | 2 |
| 6 | 32 | m | 59 | 0 | 6 | 2 | 4 | 3 |
| 7 | 30 | m | 22 | 0 | 5 | 1 | 3 | 2 |
| 8 | 36 | f | nd | 0 | 4 | 1 | 3 | 0 |
| 9 | 24 | f | nd | 0 | 1 | 0 | 4 | 3 |
| 10 | 33 | m | 27 | 0 | 2 | 0 | 1 | 0 | a Relative ELISA Units/ml
b nd = not determined

Results Obtained During the Priority Year.

The cDNA encoding rAsp f8 was isolated and expressed in the same way as rAsp f4 and rAsp f6 and corresponds to the coding sequence for a $P_2$ acidic ribosomal protein and represents therefore a classical non-secreted protein. Although not tested clinically, the protein represents an IgE-binding protein when evaluated in ELISA according to the procedures given above. All results so far obtained from ELISA show that rAsp f8 is highly specific for sera of patients suffering from ABPA. None of the 35 allergic asthmatics tested showed detectable levels of rAsp f8-specific IgE (2.3±0.4 EU/ml) which is not statistically different from the value obtained for the 20 healthy individuals (1.2±0.6 EU/ml). In contrast, 17 of the 54 patients suffering from ABPA (31%) were clearly sensitized to rAsp f8. The mean EU/ml value of the whole sample corresponds to 8±14 of the overalls sensitization involving all *A. fumigatus*-sensitized patients (allergies+ABPA, n=89) corresponds to 19% (EU/ml 5.4±12). However. This new ABPA-specific allergen do not contribute to the improvement of the differential diagnosis of ABPA because all patients recognizing rAsp f8 already recognize rAsp f4, rAsp f6 or both of them.

The DNA sequence for rAsp f8 is shown as SEQ ID NO 5 and the corresponding amino acid sequence as SEQ ID NO 6. The sequences are preliminary determined and may be incorrect at up to 10 positions, e.g. positions 92, 94, 108, 156 and 183 in the DNA sequence for rAsp f8 have not been finally confirmed.

REFERENCE LIST

1. Levitz et al., Clin. Infect. Dis. 14 (1992) 37–42
2. Lyman et al., Infect. Immun. 62 (1994) 1489–1493
3. Roilides et al., Infect. Immun. 61 (1993) 1185–1193
4. Romani et al., Curr. Opin. Immunol. 7 (1995) 517–523
5. Kurup et al., Clin. Microbiol. Rev. 4 (1991) 439–456
6. Borga et al., Ph.D. Thesis, Karolinska Institute, Repro Print AB, Stockholm, 1980
7. Yunginger et al., Pediatr. Clin. North Am. 30 (1988) 795–805

8. Greenberger et al., J. Allergy Clin. Immunol. 81 (1988) 646–650
9. Greenberger et al., Ann. Allergy 65 (1986) 444–452
10. Ricketti et al., J. Allergy Clin. Immunol. 71 (1983) 541–545
11. Greenberger et al., J. Allergy Clin. Immunol. 74 (1984) 645–653
12. Patterson et al., In: Allergic bronchopulmonary aspergillosis. Eds Patterson et al., Ocean Side Publ., Propvidence J., Rhode Island, (1995) 29–33
13. Richeson et al., Postgrad. Med., 88 (1988) 217–219
14. Henderson et al., Thorax 68 (1968) 513–515
15. Basica et al., J. Allergy Clin. Immunol. 68 (1981) 98–102
16. Laufer et al., J. Allergy Clin. Immunol. 73 (1984) 44–48
17. Nikolaizik et al., Pediatr. Allergy Immunol. 2 (1981) 83–86
18. Patterson et al., E. Am. J. Med. 54 (1976) 16–22
19. El-Dahr et al., Am. J. Respir. Crit. Care Med. 150 (1994) 1513–1518
20. Mintzer et al., Radiology 127 (1978) 301–307
21. Neeld et al. Am. Rev. Respir. Dis. 142 (1990) 1200–1205
22. Panchal et al., Eur. Respir. J. 7 (1994) 1290–1293
23. Roseberg et al., Ann. Intern. Med. 86 (1977) 405–414
24. Patterson et al., Ann. Intern. 96(1982) 286–291.
25. Nelson et al., Am. Rev. Respir. Dis. 120 (1979) 863–873
26. Greenberger et al., In: Allergy, principle and practice. Eds. Middleton et al., The C V. Mosby Company, (1988) 1219–1236
27. Kurup et al., Am. J. Clin. Pathol. 69 (1978) 414–417
28. Kauffman et al., J. Allergy Clin. Immunol. 73 (1984) 567–573
29. Creticos et al., Clin. Rev. Allergy 4 (12986) 355–361
30. Piechura et al. Immunol. 49 (1983) 657–665
31. Karlsson-Borga et al., J. Immunol. Meth. 136 (1991) 91–102
32. Baur et al., J. Allergy Clin. Immunol. 83 (1989) 839–844
33. Berntstein et al. J. Allergy Clin. Immunol. 86 (1990) 532–539
34. Müllbacher et al., Proc. Natl. Acad. Sci. USA 81 (1984) 3835–3837
35. Williams et al., J. Allergy Clin. Immunol. 89 (1992) 738–745
36. Leser et al., J. Allergy Clin. Immunol. 90 (1992) 589–599
37. Menz et al., Pneumologie, in press.
38. Dreborg et al., Position Paper. Allergy 48 (1993) 49–82
39. Moser et al., J. Immunol. 149 (1992) 454–460
40. Crameri et al., Recombinante Allergene und ihr Potential für die allergologische Diagnostik. Pneumologie, in press
41. King et al., J. Allergy Clin. Immunol. 96 (1995) 5–14
42. Hermann et al., Recombinant allergens from *Aspergillus fumigatus* and *Candida boidinii* share IgE-bindin epitopes (submitted 1996)
43. Crameri et al., J. Exp. Med. 184 (1996) 265–270
44. Mflller et al., J. Allergy Clin. Immunol. 96 (1995) 395–402
45. Kang et al., Proc. Natl. Acad. Sci. USA 88 (1991) 4363–4366
46. Suter et al., In: Phage display of peptides and proteins. Eds. Kay et al., Academic Oress, Inc, (1966) 187–205
47. Barbas III et al., Comp. Meth. Enzymol. 2?? (1991) 119–124
48. Pernelle et al., Biochemistry 32 (1993) 11682–11687
49. Crameri et al. Gene 137 (1993) 69–75
50. Diolez et al., J. Bacteriol. 167 (1986) 400–403
51. Crameri et al., Eur. J. Biochem. 226 (1994) 53–58
52. Crameri et al., Int. Arch. Allergy Immunol. 110 (1996) 41–45
53. Crameri. pJuFo: a phage surface display system for cloning genes based on protein-ligand interaction. In: Gene Cloning and Analysis: Current Innovations. Ed. Schaeffer. Horizon Scietific Press (in press)
54. Butler et al., In: Structure of Antigens Vol 1. Ed: van Regenmortel. CRC Press, Boca Raton, Fla., (1992) 208–259
55. Butler et al., Mol. Immunol. 30 (1993) 1165–1175
56. Dierks et al., Mol. Immunol. 23 (1986) 403–411
57. Suter et al., Immunol. Letter 13 (1986) 313–316
58. Sanger et al., Proc. Natl. Acad. Sci. USA 74 (1977) 5463–5467
59. Moser et al., Agents and Actions 43 (1993) 131–137
60. Hochuli et al., J. Chromatogr 411 (1987) 177–184
61. Hochuli et al., Biol/Technol. 6 (1988) 1321–1325
62. Stüber et al., In: Immunologicas: Lefkovitz et al. Academic Press, New York (1990) 121–152
63. Hochuli et al., In: Genetic Engineering, Principles and Methods. Ed: Seltow, Plenum Press, New York (1990) 87–98
64. Dudler et al., Biochim. Biophys. Acta 1165 (1992) 201–210
65. Schenk et al., Bio/Techniques 19 (1995) 196–200
66. Moser et al., J. Allergy Clin. Immunol. 93 (1994) 1–11
67. Nikolaizik et al., Skin test reactivity to recombinant *Aspergillus fumigatus* allergen I/a in patients with cystic fibrosis. Int. Arch. Allergy Immunol. (in press).
68. Butler, Immunochemistry of solid-phase immunoassays. Boca Raton, CRC Press (1991).
69. Held et al., Scand. J. Immunol. 29 (1989) 203–209
70. Sheffer et al., J. Allergy Clin. Immunol. 88(1989) 425–434
71. Nikolaizik et al., Am. J. Respir. Crit. Care Med 152 (1995) 634–639
72. Hottiger et al., Nucleic Acids Res. 23 (1995) 736–741
73. Crameri et al., Display of cDNA libraries on phage surface: an efficient strategy for selective isolation of clones expressing allergens. In: Molecular Biology of Allergens and the Atopic Response. Eds: Sehon et al., Plenum Publishing Corporation. Submitted 1996.
74. Kerpolla et al., Curr. Opin. Struct. Biol. 1 (1991) 71–79
75. Abate et al., Proc. Natl. Acad. Sci. USA 87 (1990) 1032–1036.
76. Disch et al., Int. Arch. Allergy Immunol. 108 (1995) 89–94
77. Mertens et al., Bio/Technology 13 (1995) 175–197
78. Mofatt et al., J. Mol. Biol. 189 (1986) 113–130
79. Little et al., J. Allergy Clin. Immunol. 98 (1996) 55–63
80. Crameri et al., Eur. J. Biochem. 226 (1995) 460–461
81. Crameri et al., Clin. Exp. Allergy 26 (1996) in press "Automated specific IgE assay with recombinant allergens: evaluation of the recombinant Aspergillus fumigatus allergen I in the Pharmacia CAP System"
82. Suter et al., In: Molecular Biology and Immunology of Allergens. Eds: Kraft et al., Boca Raton, CRC Press (1993) 267–269
83. Banerjee et al., J. Lab. Clin. Med. 127 (1996) 253–262
84. Banerjee et al., Asian Pacific J. All. Immunol. 8 (1990) 13–18

What is claimed is:

1. A method for the diagnosis of ABPA in a human individual, comprising determining if the individual carries antibodies reactive with one or more ABPA-related recombinant allergens, which one or more ABPA-related recombinant allergens discriminate between ABPA and allergic sensitization to A. fumigatus and wherein the one or more allergens are selected from the group consisting of rAsp f4 and rAsp f6, and ABPA-related fragments thereof which bind with IgE or IgG antibody.

2. A method for the diagnosis of ABPA in a human individual, comprising determining if the individual carries antibodies reactive with one or more ABPA-related recombinant allergens, which one or more ABPA-related recombinant allergens discriminate between ABPA and allergic sensitization to A. fumigatus and wherein the one or more allergens are selected from the group consisting of rAsp f8 and ABPA-related fragments thereof which bind with IgE or IgG antibody.

3. The method according to claim 1, wherein an in vitro immunoassay is carried out on a fluid sample from the individual for the determination of the level of antibodies diredted towards said recombinant allergens.

4. The method according to claim 1, wherein antibodies of the IgE class are determined.

5. The method according to claim 1, wherein an in vivo test is carried out in the individual.

6. The method according to claim 5, wherein the test is a skin test involving placing said one or more ABPA-related recombinant allergens in the skin of the patient.

7. The method according to claim 2, wherein an in vitro immunoassay is carried out on a fluid sample from the individual for the determination of the level of antibodies directed towards said recombinant allergens.

8. The method according to claim 7, wherein antibodies of the IgE class are determined.

9. The method according to claim 2, wherein an in vivo test is carried out in the individual.

10. The method according to claim 9, wherein the test is a skin test involving placing said one or more ABPA-related allergens in the skin of the patient.

11. The method according to claim 3, wherein antibodies of the IgE class or IgG class, or subclasses thereof, are determined.

12. The method according to claim 7, wherein antibodies of the IgE class or IgG class, or subclasses thereof, are determined.

13. A method for the diagnosis of ABPA in a human individual, comprising determining if the individual carries antibodies reactive with one or more ABPA-related recombinant allergens, which one or more ABPA-related recombinant allergens discriminate between ABPA and allergic sensitization to A. fumigatus, wherein the allergen is derived from A. fumigatus and wherein the one or more allergens are selected from the group consisting of rAsp f4 and rAsp f6, and ABPA-related fragments thereof which bind with IgE or IgG antibody.

14. The method according to claim 13, wherein the one or more allergens are selected from the group consisting of rAsp f4 and rAsp f6.

15. A method for the diagnosis of ABPA in a human individual, comprising determining if the individual carries antibodies reactive with one or more ABPA-related recombinant allergens, which one or more ABPA-related recombinant allergens discriminate between ABPA and allergic sensitization to *A. fumigatus*, wherein the allergen is derived from *A. fumigatus* and wherein the one or more allergens are selected from the group consisting of rAsp f8, and ABPA-related fragments thereof which bind with IgE or IgG antibody.

16. The method according to claim 15, wherein the allergen is rAsp f8.

17. The method according to claim 15, wherein an in vivo test is carried out in the individual.

* * * * *

UNITED STATES PATENT AND TRADEMARK OFFICE
CERTIFICATE OF CORRECTION

PATENT NO. : 6,830,891 B1
DATED : December 14, 2004
INVENTOR(S) : Reto Crameri et al.

It is certified that error appears in the above-identified patent and that said Letters Patent is hereby corrected as shown below:

Column 23,
Line 58, change "diredted" to -- directed --.

Signed and Sealed this

Twenty-sixth Day of April, 2005

JON W. DUDAS
*Director of the United States Patent and Trademark Office*